United States Patent [19]
Prewett et al.

[11] Patent Number: 5,439,684
[45] Date of Patent: Aug. 8, 1995

[54] SHAPED, SWOLLEN DEMINERALIZED BONE AND ITS USE IN BONE REPAIR

[75] Inventors: Annamarie B. Prewett, Little Silver, N.J.; Roger C. Stikeleather, Doylestown, Pa.; Simon Bogdansky, Marlboro; Robert K. O'Leary, Spring Lake, both of N.J.

[73] Assignee: Osteotech, Inc., Shrewsbury, N.J.

[21] Appl. No.: 184,306

[22] Filed: Jan. 21, 1994

Related U.S. Application Data

[60] Division of Ser. No. 809,580, Dec. 17, 1991, Pat. No. 5,298,254, which is a continuation-in-part of Ser. No. 573,458, Aug. 27, 1990, Pat. No. 5,290,558, which is a continuation-in-part of Ser. No. 410,596, Sep. 21, 1989, Pat. No. 5,073,373.

[51] Int. Cl.6 ...................... A61B 17/56; A61K 35/32
[52] U.S. Cl. .................... 424/422; 424/423; 424/549; 623/16; 514/777
[58] Field of Search .............. 424/422, 423, 549; 623/16

[56] References Cited

U.S. PATENT DOCUMENTS

| | | | |
|---|---|---|---|
| 2,968,593 | 1/1961 | Rapkin | 424/549 |
| 3,458,397 | 7/1969 | Myers et al. | 195/2 |
| 4,172,128 | 10/1979 | Thiele et al. | 424/549 |
| 4,191,747 | 3/1980 | Scheicher | 424/549 |
| 4,430,760 | 2/1984 | Smestad | 3/1.9 |
| 4,440,750 | 4/1984 | Glowacki et al. | 424/95 |
| 4,458,733 | 7/1984 | Lyons | 141/1 |
| 4,563,489 | 1/1986 | Urist | 524/21 |
| 4,595,713 | 6/1986 | St. John | 523/105 |
| 4,946,792 | 8/1990 | O'Leary | 424/549 |
| 4,994,030 | 2/1991 | Glowciewskie, Jr. et al. | 604/84 |
| 5,053,049 | 10/1991 | Campbell | 623/16 |
| 5,073,373 | 12/1991 | O'Leary | 424/423 |
| 5,162,114 | 11/1992 | Kuberasampath et al. | 424/423 |
| 5,306,304 | 4/1994 | Gendler | 623/16 |

FOREIGN PATENT DOCUMENTS

| | | |
|---|---|---|
| 0082621 | 6/1983 | European Pat. Off. . |
| 61-9059 | 3/1986 | Japan . |
| 2175807 | 10/1986 | United Kingdom . |
| 8607265 | 12/1986 | WIPO . |
| 8904646 | 6/1989 | WIPO . |

OTHER PUBLICATIONS

Covey et al., "Clinical Induction of Bone Repair With Demineralized Bone Matrix or a Bone Morphogenetic Protein", *Orthopaedic Review*, vol. XVIII, No. 8, pp. 857–863 (Aug., 1989).

Gekko et al., "Mechanism of Protein Stabilization by Glycerol: Preferential Hydration in Glycerol-Water Mixtures", vol. 20, No. 16, pp. 4667–5676 (1981).

Habal et al., "Autologous Corticocancellous Bone Paste for Long Bone Discontinuity Devects: An Experimental Approach", *Annals of Plastic Surgery*, vol. 15, No. 2, pp. 138–142 (Aug, 1985).

McLaughlin et al., "Enhancement of Bone Ingrowth by the use of Bone Matrix as a Biologic Cement", *Clinical Orthopaedics and Related Research*, No. 183, p. 255 (Mar., 1984).

*Primary Examiner*—Thurman K. Page
*Assistant Examiner*—James M. Spear
*Attorney, Agent, or Firm*—Dilworth & Barrese

[57] ABSTRACT

A shaped piece of swollen demineralized bone which can also be plasticized is provided for use in surgical bone repair.

26 Claims, 3 Drawing Sheets

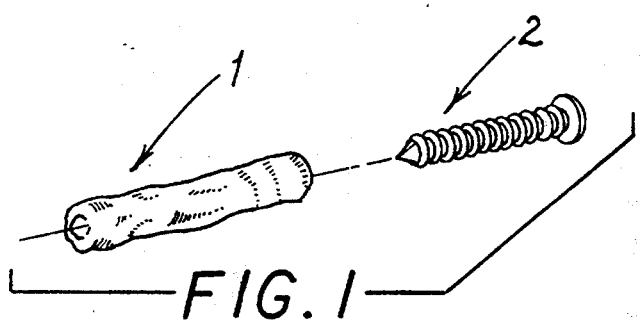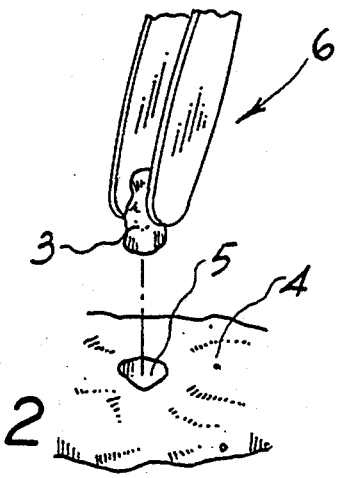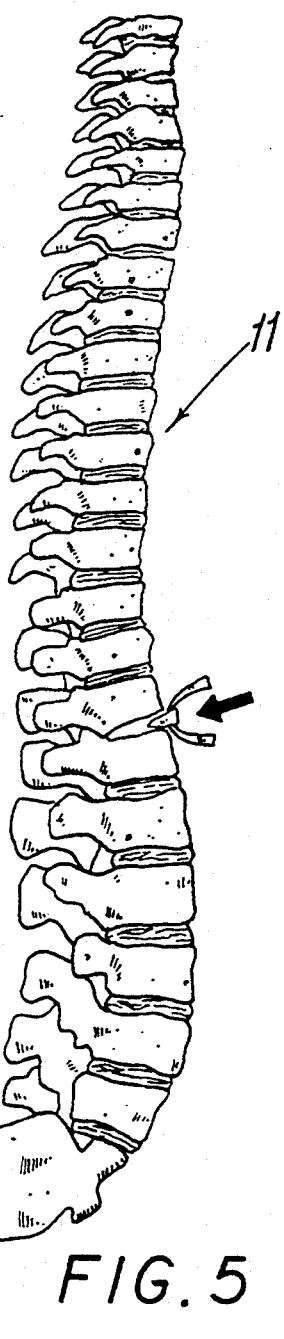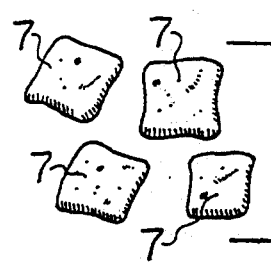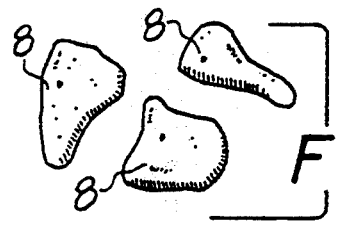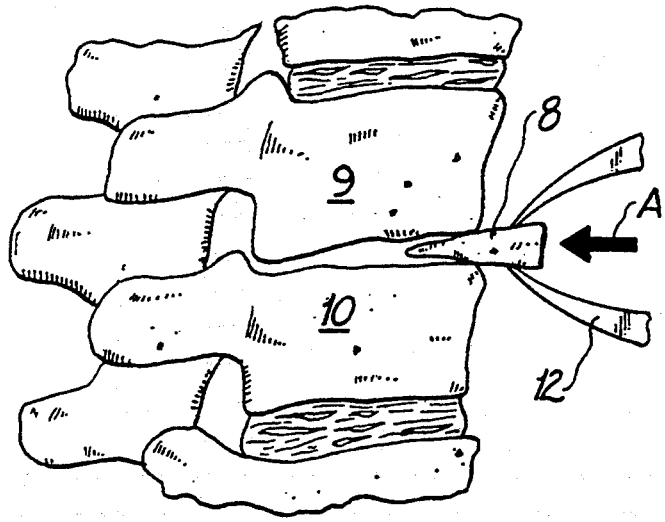

SHAPED, SWOLLEN DEMINERALIZED BONE AND ITS USE IN BONE REPAIR

CROSS REFERENCE TO RELATED APPLICATIONS

This is a divisional of application Ser. No. 07/809,580 filed Dec. 17, 1991 U.S. Pat. No. 5,298,254, which is a continuation-in-part of U.S. patent application Ser. No. 07/573,458 filed Aug. 27, 1990 U.S. Pat. No. 5,290,558 which is, in turn, a continuation-in-part of U.S. patent application Ser. No. 07/410,596 filed Sep. 21, 1989 U.S. Pat. No. 5,073,373.

BACKGROUND OF THE INVENTION

This invention relates to shaped, swollen, demineralized bone and to the use of the bone in the surgical repair of bone defects.

The use of demineralized bone powder in the repair of bone defects has been a subject of investigation for some time. Bone powder contains one or more substances, possibly bone morphogenic protein (BMP), which induce bone regeneration at the defect site. See, e.g., Covey et al., "Clinical Induction of Bone Repair with Demineralized Bone Matrix or a Bone Morphogenetic Protein", *Orthopaedic Review*, Vol. XVII, No. 8, pp. 857–863 (August, 1989).

According to Habal et al., "Autologous Corticocancellous Bone Paste for Long Bone Discontinuity Defects: An Experimental Approach", *Annals of Plastic Surgery*, Vol. 15, No. 2, pp. 138–142 (Aug. 1985), autogenous bone which has been granulated into a pastelike material and combined with autogenous blood has been used in the repair of long bone defects in dogs.

SUMMARY OF THE INVENTION

It is an object of the invention to provide swollen demineralized bone in a variety of desired shapes for use as surgical implants.

It is also an object of the invention to provide swollen, demineralized bone which has been plasticized so that the bone can be readily shaped or formed for use in a variety of surgical applications.

It is a specific object of the present invention to provide swollen demineralized bone which is optionally flexibilized and which acts as an osteoinductive and/or osteoconductive allograft upon implantation in a body.

In keeping with these and related objects of the invention, there is provided a shaped piece of swollen demineralized bone, the bone being swollen by a biocompatible swelling agent. Application of the foregoing bone to the site of a bone defect, e.g., one resulting from injury, infection, malignancy or developmental malformation, leads to rapid new bone ingrowth by one or more mechanisms such as osteogenesis, osteoconduction and osteoinduction. The bone of this invention can be readily prepared with the swelling agent along with means for disinfecting the bone before applying the bone to a bone defect site, in the form of a unitary kit. Alternatively, the bone can be prepared beforehand and stored in the swelling agent for later use, i.e., later disinfecting.

BRIEF DESCRIPTION OF THE DRAWINGS

FIG. 1 is a perspective view of one embodiment and application of the osteogenic bone of the present invention;

FIG. 2 is a perspective view of another embodiment and application of the osteogenic bone of the present invention;

FIG. 3 is a plan view of a third embodiment of the osteogenic bone of the present invention;

FIG. 4 is a plan view of a fourth embodiment of the osteogenic bone of the present invention;

FIG. 5 is a side elevational view of the application of the embodiment illustrated in FIG. 4;

FIG. 6 is an enlarged view of part of FIG. 5;

DESCRIPTION OF THE PREFERRED EMBODIMENTS

Figure 7:
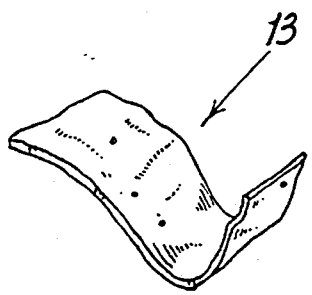
FIG. 7 is a perspective view of a fifth embodiment of the osteogenic bone of the present invention.

The demineralized bone component of the composition herein is a known type of material and is prepared in accordance with known procedures. The bone can be obtained from cortical, cancellous and/or corticocancellous autogenous, allogeneic or xenogeneic bone tissue. In general, cortical allogeneic bone tissue is preferred as the source of bone.

In a preferred bone demineralization procedure, the bone is first cut, machined and/or shaped to the desired size and dimensions followed by defatting/disinfecting and acid demineralization treatments. The operations of cutting, machining, extruding or otherwise shaping a bone piece in accordance with this invention are to be distinguished from known bone pulverizing procedures which result in bone particles not exceeding about 12 mm. in size. In the present invention, the pieces of bone are at a minimum greater than about 12 mm. in size along at least one dimension thereof, with the geometry thereof being substantially regular in that the pieces are shaped to various specific configurations such as illustrated in the accompanying figures. By contrast, particles such as chips or powders possess irregular or random geometries. The bone pieces of the present invention are of sizes which provide unified structure for easy manipulation upon implantation.

A preferred defatting/disinfectant solution is an aqueous solution of ethanol and nonionic surfactant, the ethanol being a good solvent for lipids and the water being a good hydrophilic carrier to enable the solution to penetrate more deeply into the bone. The aqueous ethanol solution also disinfects the bone by killing vegetative microorganisms and viruses. For example, the nonionic surfactant destroys the lipid toga viruses such as HIV and HBV. Ordinarily at least about 10% to 40% water (i.e., about 60% to 90% defatting agent such as alcohol) should be present in the defatting, disinfecting solution to produce optimal lipid removal and disinfection within the shortest period of time. The preferred concentration range of the defatting solution is about 60% to 85% alcohol and most preferably about 70% alcohol.

Following viricidal defatting, the bone is immersed in acid over time to effect demineralization. Acids which can be employed in this operation include inorganic acids such as hydrochloric acid and organic acids such as peracetic acid. After acid treatment, the bone is rinsed with sterile water for injection, buffered with a buffering agent to a final predetermined pH and then finally rinsed with water for injection to remove residual amounts of acid and buffering agent. The demineralized bone is then stored under aseptic conditions, i.e., in the swelling agent.

If desired, the bone can be modified in one or more ways, e.g., the porosity of the bone can be increased and/or the bone can be treated with one or more modifying agents, e.g., glutaraldehyde, as disclosed in U.S. Pat. No. 4,678,470. Another optional treatment involves augmenting or altering the bone protein content of the bone as described in U.S. Pat. Nos. 4,743,259 and 4,902,296.

Any of a variety of medically/surgically useful substances can be incorporated in the preserved, swollen bone herein, e.g., by adding the substance(s) to the bone component, e.g., by soaking or immersing the bone in a solution or dispersion of the desired substance prior to adding the swelling agent, by adding the substance(s) to the swelling agent, i.e., polyhydroxy compound component prior to immersing the bone therein or by adding the substances directly to the swelling agent after the bone has been incorporated therein. Alternatively, these medically/surgically useful substances can be added to the bone after the bone has been removed from the swelling agent, e.g., by dipping the preserved and swollen bone in a sterilizing solution containing one or more of these medically/surgically useful substances.

Medically/surgically useful substances which can be readily incorporated in the bone of this invention include, e.g., collagen and insoluble collagen derivatives, hydroxy apatite, etc., and soluble solids and/or liquids dissolved therein, e.g., antiviricides, particularly those effective against HIV and hepatitis; antimicrobials and/or antibiotics such as erythromycin, bacitracin, neomycin, penicillin, polymyxin B, tetracyclines, viomycin, chloromycetin and streptomycins, cefazolin, ampicillin, azactam, tobramycin, clindamycin and gentamycin, etc.; amino acids, magainins, peptides, vitamins, inorganic elements, co-factors for protein synthesis; hormones; endocrine tissue or tissue fragments; synthesizers; enzymes such as collagenase, peptidases, oxidases, etc.; polymer cell scaffolds with parenchymal cells; surface cell antigen eliminators; angiogenic drugs and polymeric carriers containing such drugs; collagen lattices; biocompatible surface active agents; antigenic agents; cytoskeletal agents; cartilage fragments, living cells such as chondrocytes, bone marrow cells, mesenchymal stem cells, natural extracts, tissue transplants, bioadhesives, bone morphogenic proteins (BMPs), transforming growth factor (TGF-beta), insulin-like growth factor (IGF-1); growth hormones such as somatotropin; bone digestors; antitumor agents; fibronectin; cellular attractants and attachment agents; immunosuppressants; permeation enhancers, e.g., fatty acid esters such as laureate, myristate and stearate monoesters of polyethylene glycol, enamine derivatives, alpha-keto aldehydes, etc.; nucleic acids; and, bioerodable polymers such as those disclosed in U.S. Pat. Nos. 4,764,364 and 4,765,973 and European Patent Application 168,277. The amounts of such optionally added substances can vary widely with optimum levels being readily determined in a specific case by routine experimentation.

To provide the swollen demineralized bone piece of this invention, the demineralized bone is contacted with a biocompatible swelling agent for a period of time sufficient to cause swelling of the piece. A preferred swelling agent and one which also serves as a preservative for the bone is any one or mixture of biocompatible liquid polyhydroxy compounds hereinafter identified. These compounds can be hypertonic, isotonic or hypotonic and are thought to function by penetrating and permeating the demineralized bone matrix and causing polymerized collagen crystallites contained therein to swell and the fibers contained within the matrix to become filamentous.

The expressions "liquid polyhydroxy compound" and "liquid polyhydroxy compound derivative" as employed herein are intended to include those compounds of this type which in the pure or highly concentrated state and at ambient temperature, e.g., 15°-40° C., are flowable liquids. The expressions "solid polyhydroxy compound" and "solid polyhydroxy compound derivative" as employed herein are intended to include those compounds of this type which in the pure or concentrated state and at ambient temperature are normally solid or semi-solid but are soluble in a suitable solvent, e.g., water, physiological saline, ethanol, glycerol, glucose, propylene glycol, polyethylene glycol of from 200–1000 molecular weight, etc., or mixtures thereof, to provide a liquid composition.

Useful polyhydroxy swelling agents possess from 2 to about 18 carbons and include such classes of compounds as the acyclic polyhydric alcohols, non-reducing sugars, sugar alcohols, sugar acids, monosaccharides, disaccharides, water-soluble or water dispersible oligosaccharides, polysaccharides and known derivatives of the foregoing. Specific polyhydroxy compounds include ethylene glycol, diethylene glycol, triethylene glycol, 1,2-propanediol, trimethylolethane, trimethylopropane, erythritol, pentaerythritol, polyalkylene glycols such as the polyethylene glycols, xylitol, sorbitol, mannitol, dulcitol, arabinose, xylose, ribose, adonitol, arabitol, rhamose, inositol, fructose, galactose, glucose, mannose, sorbose, sucrose, maltose, lactose, maltitol, lactitol, stachyose, maltopentaose, cyclomaltohexaose, carrageenan, agar, alginic acid, guar gum, gum tragacanth, locust bean gum, gum arabic, xanthan gum, amylose, mixtures of any of the foregoing, and the like.

Derivatives of the foregoing polyhydroxy compounds, in particular, ester derivatives thereof, are also useful as swelling agents. For example, liquid and solid monoesters and diesters of glycerol can be used to good effect, the solid esters being dissolved up to the limit of their solubilities in a suitable vehicle, e.g., propylene glycol, glycerol, polyethylene glycol of 200–1000 molecular weight, etc. Liquid glycerol esters include monacetin and diacetin and solid glycerol esters include such fatty acid monoesters of glycerol as glycerol monolaurate which is preferred, glyceryl monopalmitate, glyceryl monostearate, etc. An especially preferred carrier herein comprises glyceryl monolaurate dissolved in glycerol or a 4:1 to 1:4 mixture of glycerol and propylene glycol.

Of the foregoing polyhydroxy compounds, glycerol and its liquid monoesters and diesters, e.g., monacetin and diacetin, fructose, glucose and sucrose, and mixtures thereof are preferred. Where the polyhydroxy compound is a solid, e.g., sucrose, a solvent such as water, glycerol, polyethylene glycol of from 200–1000 average molecular weight, or mixture thereof is used to preferably provide a flowable solution or paste of the compound.

As previously indicated, the bone composition of this invention can be freshly demineralized just prior to swelling by mixing the demineralized bone, swelling agent and optional component(s) in any suitable sequence of separate mixing operations or all at once. Thus, the optional ingredient(s) can first be applied to the bone and thereafter the bone can be combined with the swelling agent, the bone can be mixed with the swelling agent followed by addition of the optional ingredient(s) or the optional ingredients can be added to the swelling agent followed by inclusion of the demineralized bone. Variations of these sequences of mixing operations are, of course, possible.

The amount of bone which can be incorporated into the swelling agent of this invention can vary widely with the amounts of from about 5 to about 90 weight percent, and preferably from about 20 to about 80 weight percent, being entirely suitable in most cases, the balance of the composition being made up of swelling agent. Furthermore, the optional ingredient(s) can be added to the bone after the bone has been removed from the swelling agent, i.e., just prior to implantation into a bone defect site. For example, the swollen bone can also be dipped in a solution containing these optional ingredients after removal from the swelling agent.

To facilitate on-site preparation of the bone for implantation into a bone defect site, the bone in the swelling agent and a plasticizing and/or disinfecting solution (the latter containing any of the optional ingredients identified above) can be stored in separate packages or containers under sterile conditions as part of a kit, with the bone removed from the swelling agent and brought together with the disinfecting solution in intimate admixture at the moment of use for immediate application to a bone defect site employing any suitable means, e.g., a syringe, spatula, etc. Alternatively, the demineralized bone can be prepared well in advance and stored in the swelling agent under sterile conditions until required for use, when the bone can be removed from the swelling agent and then dipped into a separately-provided disinfecting solution.

More specifically, as noted supra, the demineralized bone, after removal from the swelling agent and prior to implantation into a body such as into a bone defect site, is preferably contacted with an aqueous composition, e.g., a plasticizing and disinfecting solution to ensure total removal of vegetative organisms of the bone upon implantation in a body. The disinfecting solution itself is preferably aqueous and can include any of the optional ingredients enumerated supra. A preferred composition of the disinfecting solution is an aqueous solution including from about 250 to about 1000 mg/ml, and most preferably from about 500 to about 600 mg/ml disinfectant. The disinfectant includes antibiotics and other bactericides and/or bacteriostats. More particularly, the disinfectant is selected from at least one of bacitracin, polymyxin B, neomycin, sodium cefazolin and gentamicin sulfate, with gentamicin sulfate being especially preferred.

The disinfecting solution can be applied to the bone in any number of ways, e.g., by spraying, by brushing, by dipping the bone into the solution, etc. As noted supra, the disinfecting solution and preserved, swollen bone can be constituted together in the form of a kit such as shown in U.S. Pat. No. 4,994,030 the contents of which are incorporated by reference herein. In this regard, the bone is stored in one vessel along with the swelling medium which is drained out of the vessel, e.g., through a double-ended needle puncturing the vessel. Then, the disinfecting/plasticizing medium contained in another vial, is introduced into the vessel containing the preserved, swollen bone, e.g., by way of a double-ended needle illustrated in FIG. 7 of U.S. Pat. No. 4,994,030. U.S. Pat. No. 4,994,030 also discloses suitable disinfecting medium for the bone.

After the demineralized bone has been stored in the swelling agent for some time, the swollen bone becomes fairly rigid because the swelling medium, i.e., liquid polyhydroxy compound, is extremely hydrophilic and hypertonic and absorbs water out from the demineralized bone. While the water absorption serves to swell the demineralized bone collagen matrix upon storage over a period of time, it also renders the swollen bone fairly rigid. However, upon contact with the aqueous disinfecting solution, water is restored into the demineralized bone tissue which increases the plasticity of the same (i.e., the flexibility or resilient nature thereof). Therefore, the flexibility of the demineralized bone existing right after demineralization is restored, while at the same time the bone has been suitably swollen for a length of time and is now in condition for being pressed and/or shaped e.g., into a surgical implant site.

The bone of the present invention can be machined, cut, extruded, and/or otherwise formed into any desired shape or dimension for implantation into a body. For example, the bone can be sliced into a very thin sheet, cut into the shape of a disc, ring, cube, cylinder etc., or sliced and wrapped into a tubular shape. While such shaping can be carried out before the bone is preserved and swelled, the bone can first be preserved and swelled and then appropriately cut, shaped, or even extruded after removal from the swelling agent and before implantation into a body.

More specifically, several examples of suitable forms of the demineralized bone for implantation into a body are shown in FIGS. 1–18. FIG. 1 illustrates the demineralized bone having been sliced and wrapped into a substantially tubular shape to form a sleeve or stabilizer 1 for a screw 2. The screw 2 is inserted into the sleeve or stabilizer 1 and then introduced into an orifice within bone to affix a plate or other osteoprosthetic implant to the bone. This immediately improves the screw's holding power. Then, over time, the screw becomes calcified within the bone. FIG. 2 illustrates the demineralized bone having been cut into a substantially cylindrical shape to form a plug 3 to fill defects within bone. For example, the plug 3 can be used to fill a hole 5 left in bone 4 by removal of a screw such as screw 2 of FIG. 1. The plug 3 is introduced into the hole 5 by way of forceps 6 as illustrated in FIG. 2.

Figure 15:
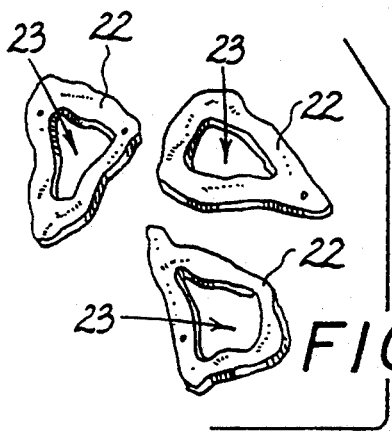
FIG. 15 is a plan view of a ninth embodiment of the osteogenic bone of the present invention.

FIG. 3 illustrates the demineralized bone having been cut into four substantially thin parallelepipeds which are wafer-like and are termed pledgets 7. These pledgets 7 can be substantially rectangular. FIG. 4 illustrates the demineralized bone having been cut into several wedges 8. Both pledgets 7 and wedges 8 can be used as invertebral support blocks. For example, FIGS. 5 and 6 illustrate one of the wedges 8 being inserted between adjacent vertebrae 9 and 10 in a spinal column 11 in place of an invertebral disk that has been removed. More specifically, FIG. 6 illustrates insertion of the wedge 8 in the direction of arrow A by forceps 12. Wedges 22, which are cross-sections of fibula, are illustrated in FIG. 15 which have been prepared from corticocancellous bone, with the cancellous centers having been removed to leave openings 23 and with just the outer cortical bone remaining.

Figure 8:
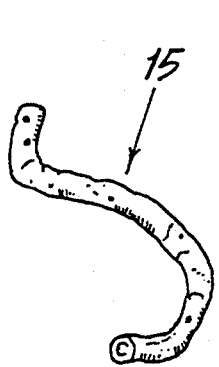
FIG. 8 is a perspective view of a sixth embodiment of the osteogenic bone of the present invention.
Figure 9:
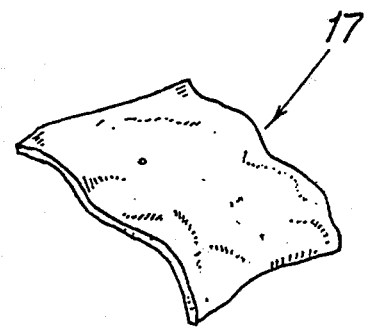
FIG. 9 is a perspective view of the seventh embodiment of the osteogenic bone of the present invention.
Figure 10:
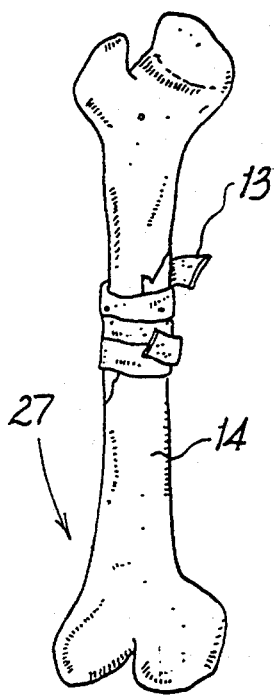
FIG. 10 is a side elevational view of the application of the embodiment illustrated in FIG. 7.
Figure 11:
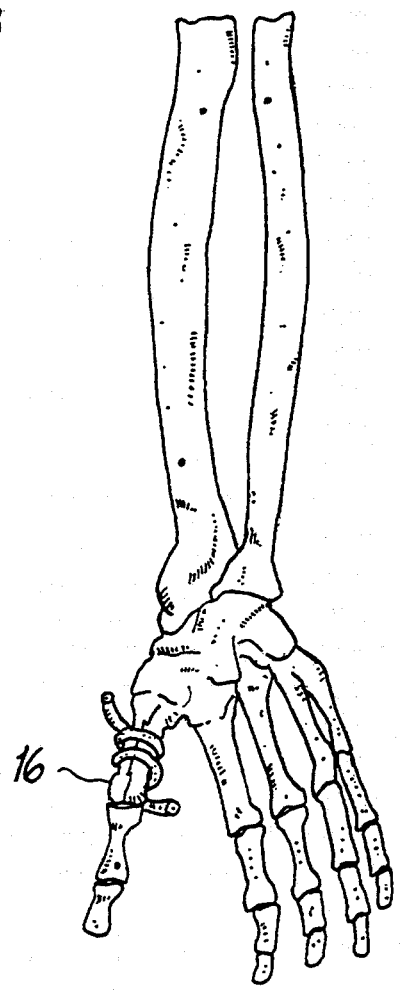
FIG. 11 is a side elevational view of the application of the embodiment illustrated in FIG. 8.
Figure 12:
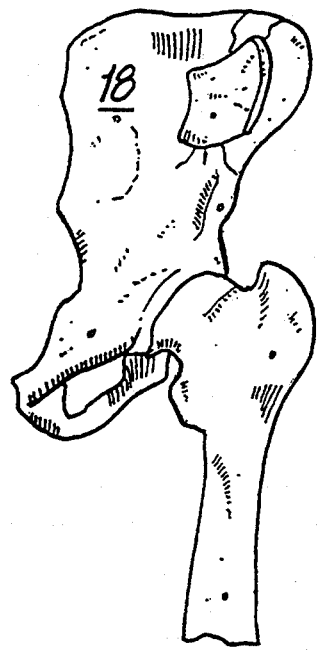
FIG. 12 is a side elevational view of the application of the embodiment illustrated in FIG. 9.
Figure 13:
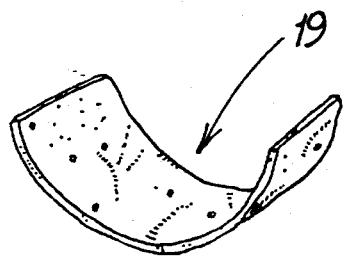
FIG. 13 is a perspective view of an eighth embodiment of the osteogenic bone of the present invention.
Figure 14:
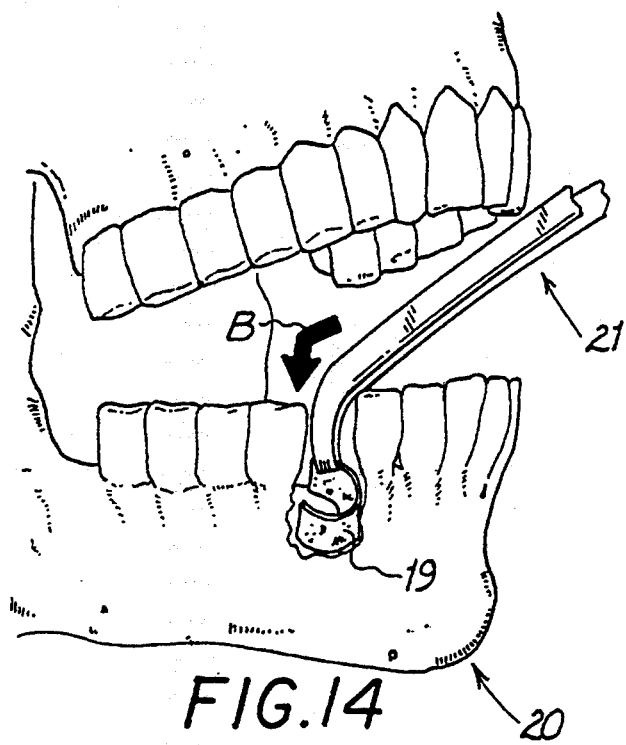
FIG. 14 is a side elevational view of the application of the embodiment illustrated in FIG. 13.

FIG. 7 illustrates the demineralized bone having been sliced into a thin flexible tape 13 which can be tightly wrapped around a fracture in a femur bone 27 as illustrated in FIG. 10. FIG. 8 illustrates the demineralized bone having been cut and/or extruded or otherwise shaped into a piece of flexible rope 15 which can be used for securing bone fractures in extremely mobile or hard-to-reach bones, such as the metacarpus bone 16 of the thumb as illustrated in FIG. 11. FIG. 9 illustrates the demineralized bone having been sliced into a thin sheet 17 which can be used to patch an injury to the ilium 18 as illustrated in FIG. 12. 0 FIG. 13 illustrates the demineralized bone having been sliced or shaped into the form of a flexible fibroblast liner 19 which can be used to prevent ingrowth of fibroblasts in an area from which bone has been excised. More particularly, when a diseased or injured tooth including the adjacent maxilla and/or mandible has been removed from the jaw 20 as illustrated in FIG. 14, it is necessary to block ingrowth of fibroblasts into the gap left by the removed tooth, at least until new bone growth permits a replacement denture to be anchored or otherwise fit into the gap. In order to prevent the ingrowth of fibroblasts which immediately begin to occur upon removal of the natural tooth, the liner 19 is introduced into the gap in the jaw 20 in the direction of arrow B and by way of forceps 21.

Figure 16:
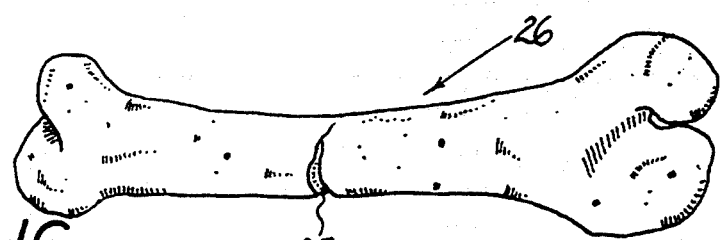
FIGS. 16–18 are schematic views illustrating a tenth embodiment of the osteogenic bone of the present invention and application thereof.
Figure 17:
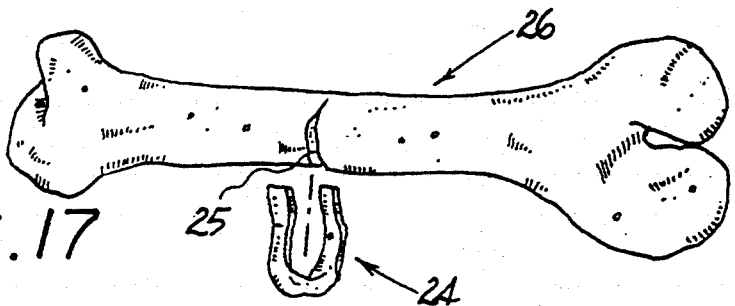
Figure 18:
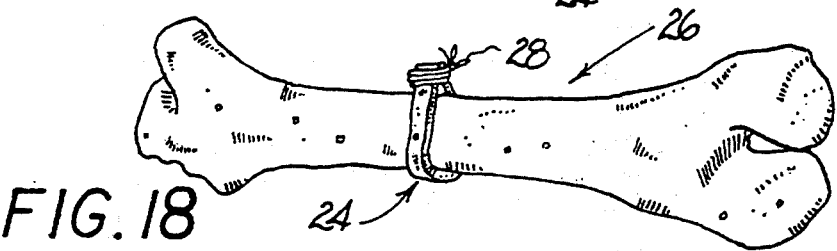

A bone clip 24 can be fashioned and used to secure a bone fracture 25 as illustrated in FIGS. 16–18 respectively. More particularly, the clip 24, which is substantially in the shape of a U, is inserted over the location of the fracture 25 of a femur bone 26 as illustrated in FIG. 17, with the ends of the clip then being tied together, e.g., with a suture 28, as illustrated in FIG. 18, thus securing the fracture.

Thus, the demineralized, swollen and plasticized bone of this invention can be applied to the bone defect in a variety of ways. Among the bone repair applications for which the use of the treated bone in accordance with the present invention is eminently suited are: standard or custom arthroplasty prosthesis; reconstruction of skeletal or other osseous defects; enhancing or augmenting the effectiveness of internal and external fixation devices, bone plates, etc., as a replacement of corticocancellous strips, and so forth.

The following examples are illustrative of the preparation of the swollen, demineralized and plasticized bone composition of the present invention.

EXAMPLE 1

Cancellous bone in an iliac crest of a human donor was drilled out, leaving behind cortical bone from the iliac crest. This cortical bone from the iliac crest was demineralized in 0.6N HCl overnight in the following manner.

500 ml of 0.6N HCl was added to a piece of the cortical bone remaining in the iliac crest and was stirred. This HCl solution was replaced with another 500 ml of 0.6N HCl solution after about 1¼ hours with stirring for approximately 14 hours. The ileum bone structure appeared to collapse. The second 0.6N HCl solution was discarded and the remaining cortical bone was washed three times with 500 ml of water for injection (WFI).

500 ml of 0.1M phosphate buffer with 0.01% sodium azide was added to the cortical ileum bone with stirring for ½ hour. The ileum bone was then removed from the phosphate buffer and dried until no more liquid could be removed from the ileum bone. The ileum bone was flexible, i.e., felt soft to the touch. This cortical ileum bone was weighed, with 2.62 g thereof being placed into a wide mouth plastic container. 60.43 g of 95% glycerol was then added to the container with continuous stirring to ensure that the cortical ileum bone remained immersed in the glycerol.

EXAMPLE 2

After being stored with the glycerol in the container of Example 1 for one day, the swollen cortical iliac bone was removed and was found to be quite rigid. Next, this bone was dipped in an aqueous disinfecting solution comprising 500 mg/ml gentamicin sulfate for 15 minutes. It was found that the flexibility returned to the demineralized bone, so that the bone can then be cut or sliced into any configuration such as shown in FIGS. 1–4, 7–9, 13, 15 and 17 which is suitable for implantation into bone defect sites.

EXAMPLE 3

The steps of the Examples 1 and 2 are repeated but with the bone being cut, sliced or shaped into various configurations just after demineralization and then immersed into the glycerol swelling agent and stored in the same.

What is claimed is:
1. A kit for swelling, disinfecting and/or plasticizing demineralized bone, said kit comprising
   (a) a first sealed vessel comprising the bone immersed in a swelling medium,
   (b) a second sealed vessel comprising disinfecting and/or plasticizing medium, and
   (c) means for accessing the interior of said first vessel for (1) draining off said swelling medium and (2) placing said first sealed vessel in open communication with said second sealed vessel containing said disinfecting and/or plasticizing medium,
   wherein said swelling medium is selected from a member of the group consisting of liquid polyhydroxy compound, liquid polyhydroxy compound ester, liquid solution of solid polyhydroxy compound, liquid solution of solid polyhydroxy compound ester and mixtures thereof, and
   the polyhydroxy compound is selected from the group consisting of acyclic polyhydric alcohols, non-reducing sugars, sugar alcohols, sugar acids, monosaccharides, disaccharides, water-soluble or water dispersible oligosaccharides, polysaccharides, polyalkylene glycols and mixtures thereof.
2. The kit of claim 1 wherein the bone is shaped.
3. The kit of claim 1 wherein the swelling medium is selected from the group consisting of glycerol, glycerol monoester and glycerol diester.
4. The kit of claim 1 wherein the swelling medium is selected from the group consisting of monosaccharide, monosaccharide ester, disaccharide, disaccharide ester, oligosaccharide, oligosaccharide ester and mixtures thereof.

5. The kit of claim 1 wherein the swelling medium is selected from the group consisting of fructose, glucose and mixtures thereof.

6. The kit of claim 1 wherein the swelling medium is a liquid solution of sucrose.

7. The kit of claim 1 wherein the swelling medium is an aqueous solution of sucrose.

8. The kit of claim 1 wherein the swelling medium is a liquid solution of a fatty acid monoester of glycerol.

9. The kit of claim 1 wherein the swelling medium is a fatty acid monoester dissolved in a solvent which is a different liquid polyhydroxy compound and/or ester thereof.

10. The kit of claim 1 wherein the swelling medium is a fatty acid monoester dissolved in a solvent selected from the group consisting of propylene glycol, glycerol, monoacetin, diacetin, liquid polyethylene glycol and mixtures thereof.

11. The kit of claim 1 wherein the swelling medium is glycerol monolaurate dissolved in a solvent.

12. The kit of claim 1 wherein the swelling medium is glycerol monolaurate dissolved in a solvent which is a different liquid polyhydroxy compound and/or ester thereof.

13. The kit of claim 1 wherein the swelling medium is glyceryl monolaurate dissolved in a solvent selected from the group consisting of propylene glycol, glycerol, monoacetin, diacetin, liquid polyethylene glycol and mixtures thereof.

14. The kit of claim 1 wherein the demineralized bone is derived from cortical bone, cancellous and/or corticocancellous autogenous, xenogeneic and/or allogeneic bone tissue.

15. The kit of claim 1 wherein the demineralized bone is derived from cortical allogeneic bone tissue.

16. The kit of claim 1 wherein a composition comprising the bone in said first vessel (a) contains from about 5 to about 90 weight percent demineralized bone and from about 10 to about 95 weight percent swelling medium.

17. The kit of claim 16 wherein said composition contains from about 20 to about 80 weight percent demineralized bone and from about 20 to about 80 weight percent swelling medium.

18. The kit of claim 1 wherein the bone contains at least one additional ingredient selected from the group consisting of antiviral agent, antimicrobial agent, antibiotic agent, amino acid, magainin, peptide, vitamin, protein synthesis co-factor, hormone, endocrine tissue, synthesizer, enzyme, polymer-cell scaffolding agent with parenchymal cells, surface cell antigen eliminator, angiogenic drug, polymeric drug carrier, collagen lattice, antigenic agent, cytoskeletal agent, mesenchymal stem cells, bone digester, antitumor agent, cellular attractant, fibronectin, growth hormone cellular attachment agent, immunosuppressant, nucleic acid, surface active agent, hydroxyapatite and penetration enhancer.

19. The kit of claim 2 wherein the bone is shaped in the form of a sheet, ring, disk, cube, cylinder or tube.

20. The kit of claim 1 wherein the bone is shaped to have substantially regular geometry and/or at least one dimension greater than about 12 mm.

21. The kit of claim 1 wherein the polyhydroxy compound possesses from 2 to about 18 carbon atoms.

22. A kit for swelling, disinfecting and/or plasticizing demineralized bone, said kit comprising
(a) a first sealed vessel comprising the bone immersed in a swelling medium,
(b) a second sealed vessel comprising disinfecting and/or plasticizing medium, and
(c) means for accessing the interior of said first vessel for (1) draining off said swelling medium and (2) placing said first sealed vessel in open communication with said second sealed vessel containing said disinfecting and/or plasticizing medium,
wherein the swelling medium is selected from the group consisting of ethylene glycol, diethylene glycol, triethylene glycol, 1,2-propanediol, trimethylolethane, trimethylopropane, erythritol, pentaerythritol, polyethylene glycols, xylitol, sorbitol, mannitol, dulcitol, arabinose, xylose, ribose, adonitol, arabitol, rhamose, inositol, fructose, galactose, glucose, mannose, sorbose, sucrose, maltose, lactose, maltitol, lactitol, stachyose, maltopentaose, cyclomaltohexaose, carrageenan, agar, alginic acid, guar gum, gum tragacanth, locust bean gum, gum arabic, xanthan gum, amylose and mixtures thereof.

23. The kit of claim 19 wherein the bone is shaped in the form of a tubular screw stabilizer or sleeve, a substantially cylindrical bone plug, a pledget, a solid or hollow wedge, a ribbon or tape, a rope, a sheet or patch, a liner or a clip.

24. The kit of claim 1 wherein said disinfecting and/or plasticizing solution comprises an aqueous solution.

25. The kit of claim 24 wherein said aqueous solution includes, in an amount suitable to disinfect said demineralized bone, a disinfectant selected from the group consisting of gentamicin sulfate, bacitracin, polymyxin B, neomycin and sodium cefazolin and mixtures thereof.

26. The kit of claim 25 wherein the swelling medium is glycerol.

* * * * *